(12) United States Patent
Hartmann et al.

(10) Patent No.: US 7,771,456 B2
(45) Date of Patent: Aug. 10, 2010

(54) INTERSPINOUS IMPLANT

(75) Inventors: Stephan Hartmann, Solothurn (CH); Armin Studer, Cham (CH)

(73) Assignee: Synthes USA, LLC, West Chester, PA (US)

( * ) Notice: Subject to any disclaimer, the term of this patent is extended or adjusted under 35 U.S.C. 154(b) by 621 days.

(21) Appl. No.: 11/704,884

(22) Filed: Feb. 8, 2007

(65) Prior Publication Data
US 2007/0191959 A1 Aug. 16, 2007

Related U.S. Application Data

(63) Continuation of application No. PCT/CH2004/000507, filed on Aug. 13, 2004.

(51) Int. Cl.
*A61B 17/70* (2006.01)
(52) U.S. Cl. .............. 606/249; 606/248; 623/17.16
(58) Field of Classification Search ........... 606/70–71, 606/280–299, 902, 99, 248–249, 279; 623/17.11–17.16
See application file for complete search history.

(56) References Cited

U.S. PATENT DOCUMENTS

| | | | |
|---|---|---|---|
| 5,645,599 A * | 7/1997 | Samani | 623/17.16 |
| 6,241,769 B1 * | 6/2001 | Nicholson et al. | 623/17.11 |
| 6,679,915 B1 * | 1/2004 | Cauthen | 623/17.11 |
| 6,712,819 B2 * | 3/2004 | Zucherman et al. | 606/86 A |
| 7,163,558 B2 | 1/2007 | Senegas et al. | |
| 7,238,204 B2 * | 7/2007 | Le Couedic et al. | 623/17.11 |
| 2002/0049497 A1 * | 4/2002 | Mason | 623/17.11 |
| 2003/0187506 A1 * | 10/2003 | Ross et al. | 623/17.13 |
| 2003/0216736 A1 * | 11/2003 | Robinson et al. | 606/61 |
| 2004/0010316 A1 * | 1/2004 | William et al. | 623/17.16 |
| 2004/0030387 A1 * | 2/2004 | Landry et al. | 623/16.11 |
| 2004/0106995 A1 | 6/2004 | Le Couedic et al. | |
| 2005/0102028 A1 * | 5/2005 | Arnin et al. | 623/17.13 |
| 2005/0125062 A1 * | 6/2005 | Biedermann et al. | 623/17.11 |
| 2005/0203512 A1 * | 9/2005 | Hawkins et al. | 606/61 |

FOREIGN PATENT DOCUMENTS

| | | |
|---|---|---|
| FR | 2 717 675 | 9/1995 |
| FR | 2717675 A1 * | 9/1995 |
| WO | WO 03/015645 | 2/2003 |
| WO | WO 2005094732 A1 * | 10/2005 |

* cited by examiner

*Primary Examiner*—Thomas C Barrett
*Assistant Examiner*—Larry E Waggle, Jr.
(74) *Attorney, Agent, or Firm*—Stroock, Stroock & Lavan, LLP (57) ABSTRACT

An intervertebral implant has two U-shaped inserts set over each other with a center piece in between. The two inserts each have an opposing base surface, two lateral side surfaces, and a contact surface. The contact surface has a channel configured to receive a spinal process of a vertebral body. The center piece has two resting surfaces corresponding respectively to each contact surfaces. The contact and resting surfaces each have corresponding structures that can engage each other such that the U-shaped inserts can each be fastened in a detachable manner to the center piece. The U-shaped inserts each have on the same lateral side surface connecting means to fasten the inserts to gripping elements of a surgical instrument. And the first and second structures can be engaged or disengaged only by the lateral side surface fitted with the connecting means.

9 Claims, 8 Drawing Sheets

INTERSPINOUS IMPLANT

CROSS-REFERENCE TO RELATED APPLICATION

This is a continuation of pending International Application No. PCT/CH2004/000507, filed Aug. 13, 2004, the entire contents of which are expressly incorporated herein by reference thereto.

FIELD OF THE INVENTION

The invention relates to an intervertebral implant that serves as a spacer for two adjacent vertebral bodies in connection with a defective intervertebral disk, which would otherwise reduce the distance between the vertebral bodies. Because such implants restore the distance between the vertebral bodies, decompression of the bevel joints also results.

BACKGROUND OF THE INVENTION

Intervertebral implants of this kind are known from FR 2 7176 675 by Taylor. This known implant comprises two rigid inserts capable of being fastened to the spinal process of the vertebral bodies and an elastic center piece between them. The inserts have at their base surfaces barbed hook-like appendices which are cast into the elastic center piece and hold the inserts together with the center piece. The disadvantage of this known implant is that during the implantation the already fully preassembled implant is inserted between the spinal processes, so that the adjacent vertebral bodies need to be widely distracted.

An intervertebral prosthesis of this kind is also known from WO 03/015645 by Mathieu. This known prosthesis comprises two elements with appendices set on the spinal processes of the vertebral bodies to be treated and on a center piece firmly connected to the processes of a part, so that each part must be inserted laterally, meaning from the other side of the spinal column.

SUMMARY OF THE INVENTION

The invention intends to offer a remedy for this situation. The object of the invention is to create an intervertebral implant that can be inserted and fastened into the intervertebral space from only one side and between two spinal processes of adjacent vertebral bodies to be treated.

The invention solves the given problem by an intervertebral implant presenting the characteristics of claim 1.

The advantages of the invention include:
  a less invasive operating process because it becomes possible to use an implant with a one-sided access;
  better control during the operating process because it becomes possible to distract the two adjacent vertebral bodies directly with the implant; and
  a shorter operating time because of the above advantages.

In one embodiment, the first and the second structures are configured in parallel and in a form-locking manner to a transversal axis set across the central axis and crossing the ventral and the dorsal lateral surfaces of the two inserts.

The first and second structures can also be configured in parallel and in a form-locking manner to the central axis.

In another embodiment, the intervertebral implant comprises locking means whereby the first and second structures can be held engaged across the central axis. This prevents the center piece from sliding out. Thanks to the automatic locking means, an operation is no longer needed.

The locking means can further be configured in a detachable fashion.

In a further embodiment, the first structures each comprise a male dovetail guide and the second structures each comprise a female dovetail guide with a longitudinal axis set across the central axis. These dovetail guides allow a free from play assembly of the three parts, so that after the implantation, the motions of the adjacent vertebral bodies are dampened by the elastic center piece.

The male and female dovetail guides may alternatively exhibit longitudinal axes extending across the transversal axis. This allows a one-sided insertion of the inserts and of the center piece.

In another embodiment, the locking means comprise screws that can be screwed into the two inserts (3;4) and blocked against shifting by inserting the male dovetail guides into the female dovetail guides. The advantage of this embodiment is in the detachable configuration of the locking means.

In a further embodiment, the female dovetail guides are closed toward the lateral side surfaces that do not have the connecting means. This means that like a locking means only one screw needs to be turned into each dovetail guide.

In still another embodiment, the male and female dovetail guides taper off toward the lateral side surfaces of the implant that do not have connecting means. This facilitates the insertion of male dovetail guides into the female dovetail guides.

The longitudinal axis of the dovetail guides may be curved. The curvature of the dovetail guides allows inserting the center piece through a rotating gripping lever, whereby the space required for the introduction can be held to a minimum.

The longitudinal axis of the dovetail guides may alternatively be straight. The advantage of this embodiment is that the dovetail guides are easy to manufacture.

In yet another embodiment, the intervertebral implant is capable of being elastically deformed. The modular construction of the intervertebral implant makes it possible to insert center pieces of different height and stiffness, so as to adapt the intervertebral implant to the anatomy in an optimal manner.

In a further embodiment, the intervertebral implant presents a progressive spring characteristic curve. The progressive spring characteristic curve ensures an adequately large elastic resilience at only a small motion of the spring. In case of shock-loads, this also allows preventing overloads on the vertebral bodies or on the intervertebral disk lying in the intervertebral space.

The locking means can be configured in a self-acting snap-in manner that allows a simpler assembly of the implant. Each female dovetail guide can be provided with a recess and each male dovetail guide can be provided with a spring element (30) having a snap-in action at a corresponding recess, so that the locking means exhibit a particularly simple design.

BRIEF DESCRIPTION OF THE DRAWINGS

The invention will be explained in yet greater detail by using the following partially simplified representations of several embodiments of the invention.

DETAILED DESCRIPTION OF THE INVENTION

Figure 1:
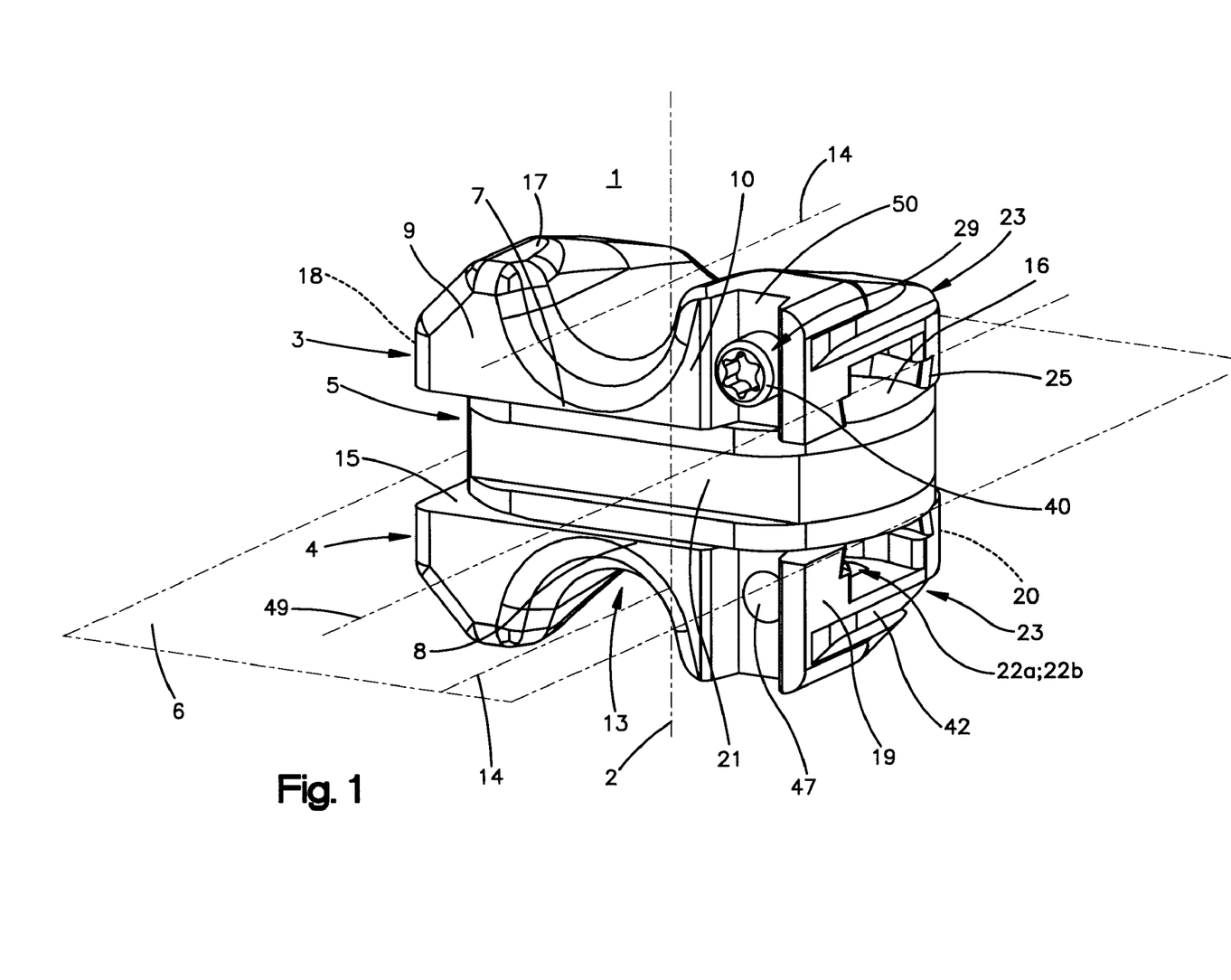
FIG. 1 is a perspective view of an embodiment of the intervertebral implant according to the invention.
Figure 2:
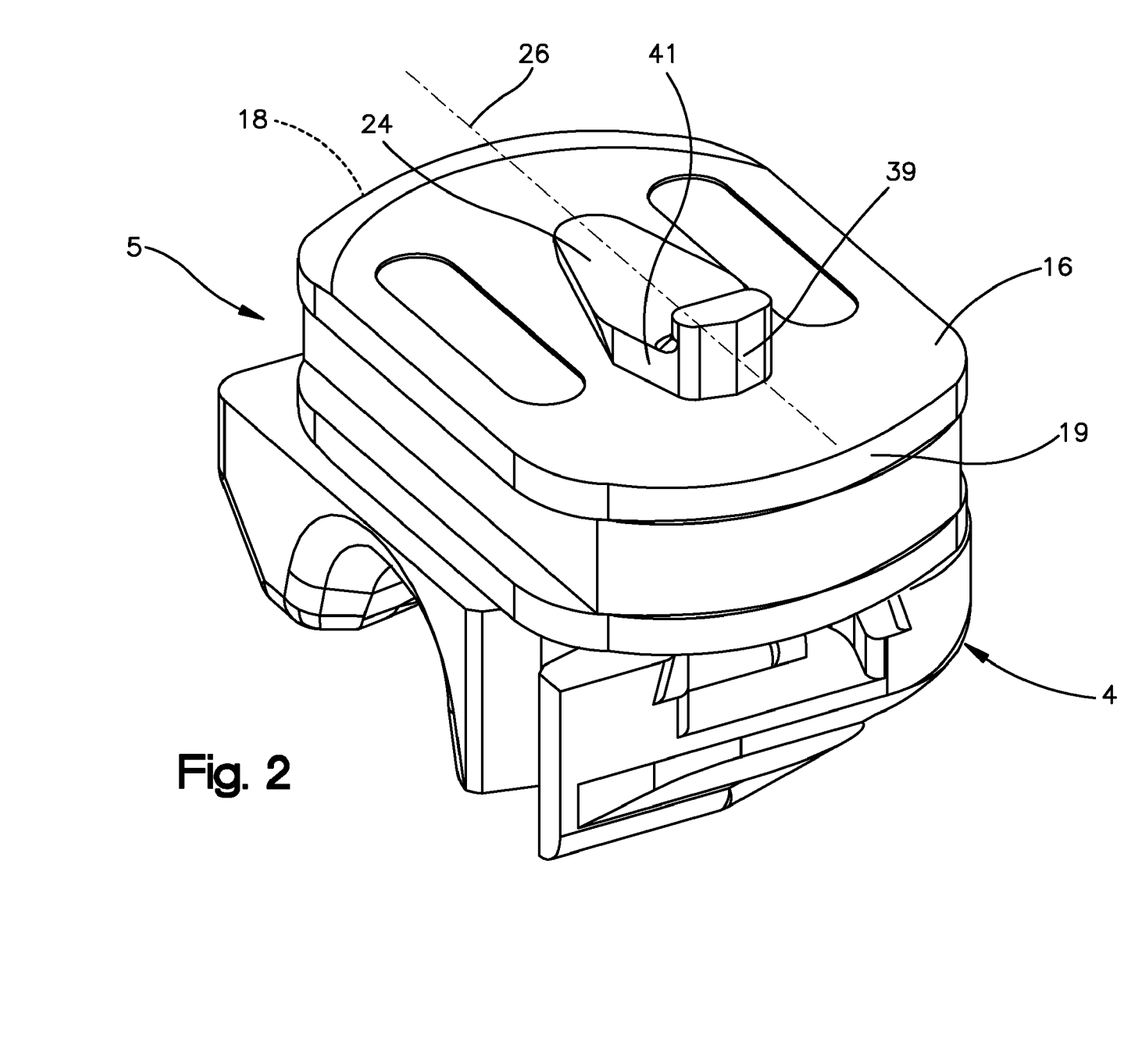
FIG. 2 is a perspective view of the center piece together with the second insert of the form of embodiment of the intervertebral implant according to the invention shown in FIG. 1.

The implant 1 shown in the FIGS. 1 and 2 comprises essentially two U-shaped inserts 3;4 set across the central axis of the intervertebral implant 1, and a center piece 5 set between them. The inserts 3;4 are set with respect to a center plane 6 set orthogonally to the longitudinal axis 2 so that the crossbars 7 of the two inserts 3,4 are set up parallel to the central plane 6 and the free extremities 11;12 of the sidebars 9:10 are pointing away from the central plane 6.

A channel delimited by two sidebars 9;10 and a crossbar 7;8 of an insert 3;4 is adapted to receive a spinal process of a vertebral body, whereby the inserts 3;4 are inserted into the intervertebral inter-vertebral space so that the crossbars 7;8 are set between the spinal processes of two adjacent vertebral bodies. The channel axes 14 of the channels 13 are set across the center axis 2 in a front-to-rear direction, meaning that they run parallel to a transversal axis 49 that crosses the ventral and the dorsal side surface 20;21 of the intervertebral implant 1. The center piece 5 is inserted between the base surfaces 15 of the crossbars 7 facing each other, whereby the resting surfaces 16 of the center piece 5 come to rest on the base surfaces 15 of the crossbars 7. The inserts 3;4 comprise lateral side surfaces 18;19 set externally on the sidebars 9;10, one each ventral side surface 20 set across the same, and one each dorsal side surface 21 and contact surface 17 fitted with one each channel 13, respectively. In order to receive the gripping elements 43 of a surgical instrument 35 (FIGS. 7 to 10), connecting means 23 are provided on the second lateral side surfaces 19.

The first and the second structures 22a;22b are set on each resting surface 16 of the center piece 5 and on each base surface 15 of the inserts 3;4. The first and second structures 22a;22b are configured as dovetail guides with one each male dovetail guide 24 on the resting surfaces 16 of the center piece (FIG. 2) and one each female dovetail guide 25 on the base surface 15 of the inserts 3;4, respectively, and are capable of connecting the inserts 3;4 with the center piece 5 in a detachable manner. The male and female dovetail guides 24;25 exhibit a longitudinal axis 26 (FIG. 2) set across the central axis 2 and lying in the central plane 6 (FIG. 2). Moreover, the dovetail guides 24;25 are oriented so that the longitudinal axis 26 (FIG. 2) runs across the channel axes 14. The female dovetail guides 25 are closed toward the first lateral side surfaces 18 of the inserts 3;4 and open toward the second lateral side surfaces 19, so that the male dovetail guides 24 can be introduced from the second lateral side surfaces 19 of the inserts 3;4 into the female dovetail guides 25. The male dovetail guides 24 are shorter than the female dovetail guides 25, so that if the center piece 5 is inserted between the inserts 3;4, one each screw 40 can be screwed into the boreholes 47 in the sidebars 10 between the rear extremity 39 (FIG. 2) of the male dovetail guide 24 fitted with a rise 41 and into the second lateral side surface 19 of the two inserts 3;4, respectively. The screw 40 acting like a locking means 29 closes the female dovetail guide 25, so that the rise 41 on the rear extremity 39 of the male dovetail guide 24 rests on the screw 40. Thanks to the male dovetail guides 24, which are secured by the screws 40 in the closed female dovetail guides toward shifting in both directions, the two inserts 3;4 are, after the two screws 40 have been screwed in, blocked with respect to the center piece 5. The sidebars 10 are conformed with recesses 50, so that the head of the screws 40 are sunk into the recesses 50 and do not project beyond the dorsal side surfaces 21 of the inserts 3;4.

Figure 9:
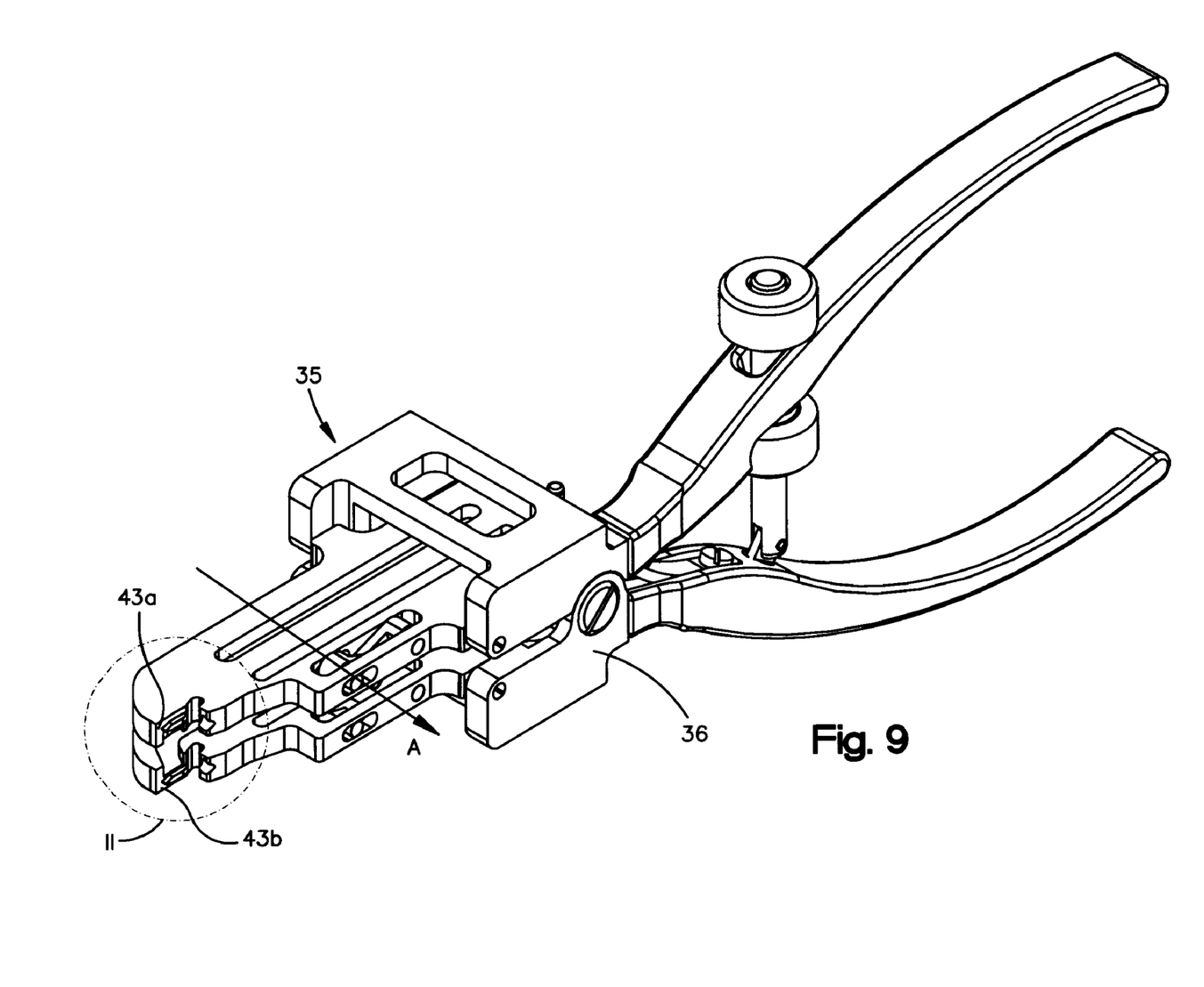
FIG. 9 is a perspective view of the two inserts of a form of embodiment of the instrument.

Grooves 42 are provided, in parallel to the channel axes 14, on the lateral side surfaces 18;19 of the two inserts 3;4. The grooves 42 are open on the dorsal side surfaces 21 and closed on the ventral side surfaces 20 and serve to receive the gripping elements 43 of a surgical instrument 35 (FIG. 9).

Figure 3:
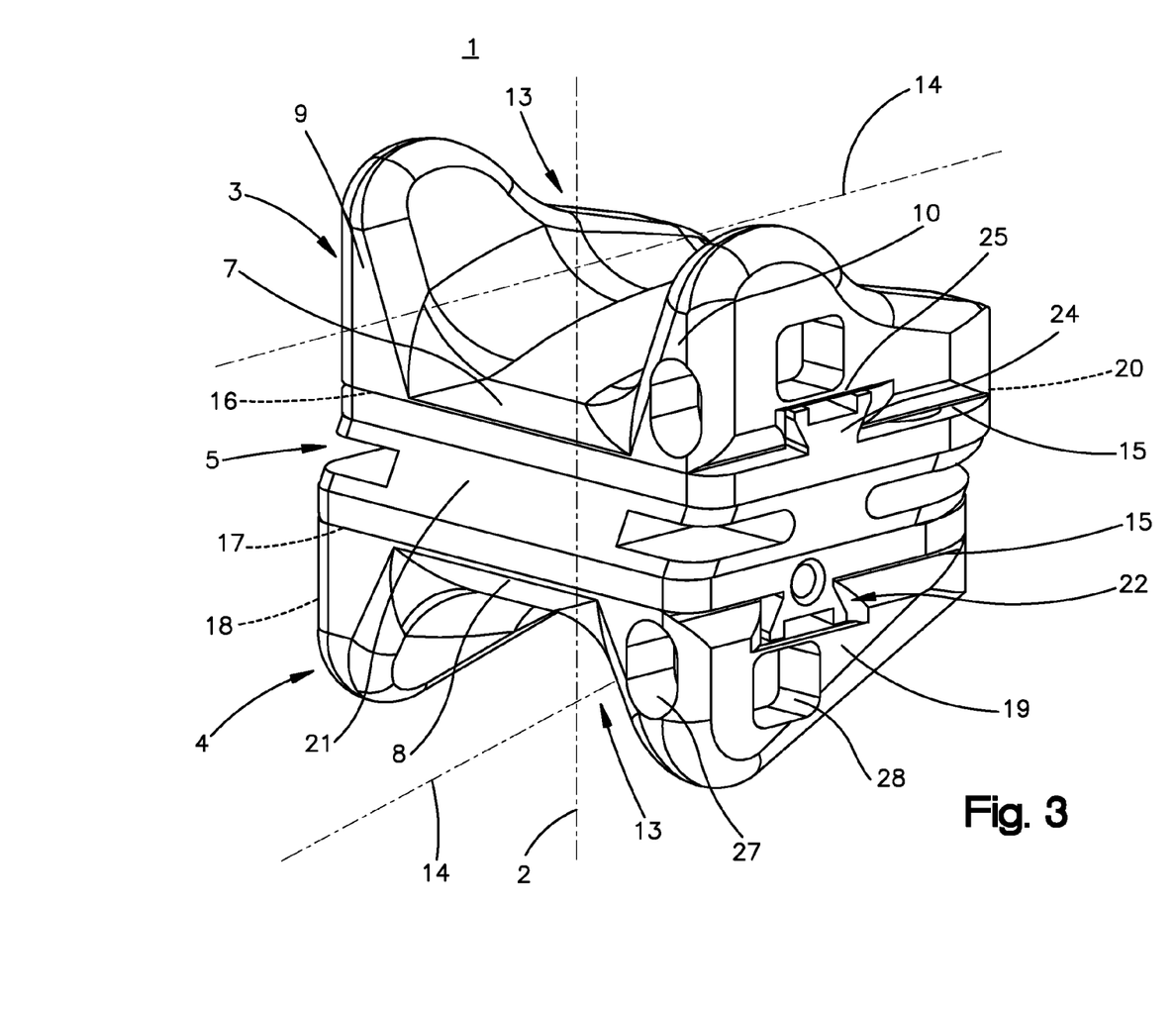
FIG. 3 is a perspective view of another embodiment of the intervertebral implant according to the invention.
Figure 4:
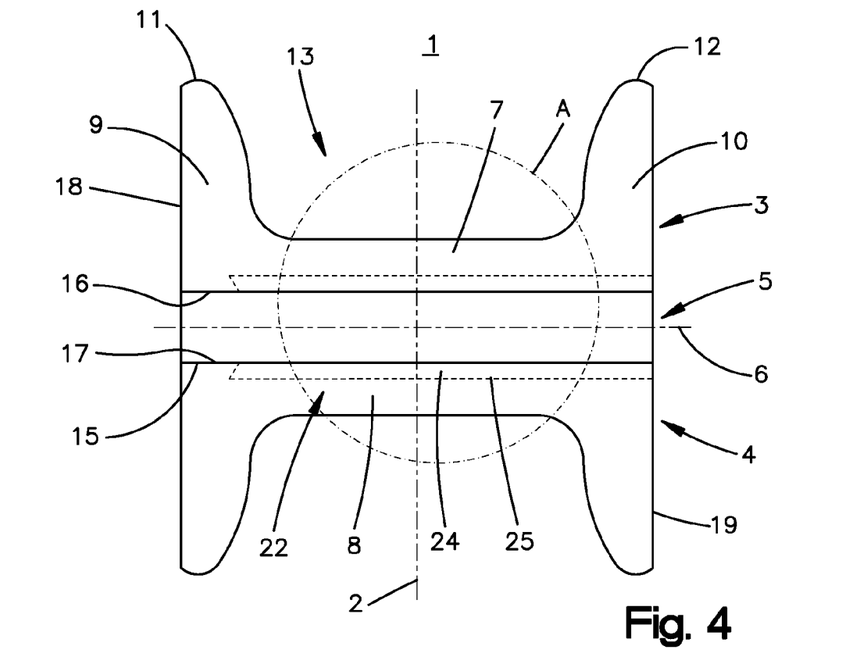
FIG. 4 is a front view of the embodiment shown in FIG. 3.
Figure 5:
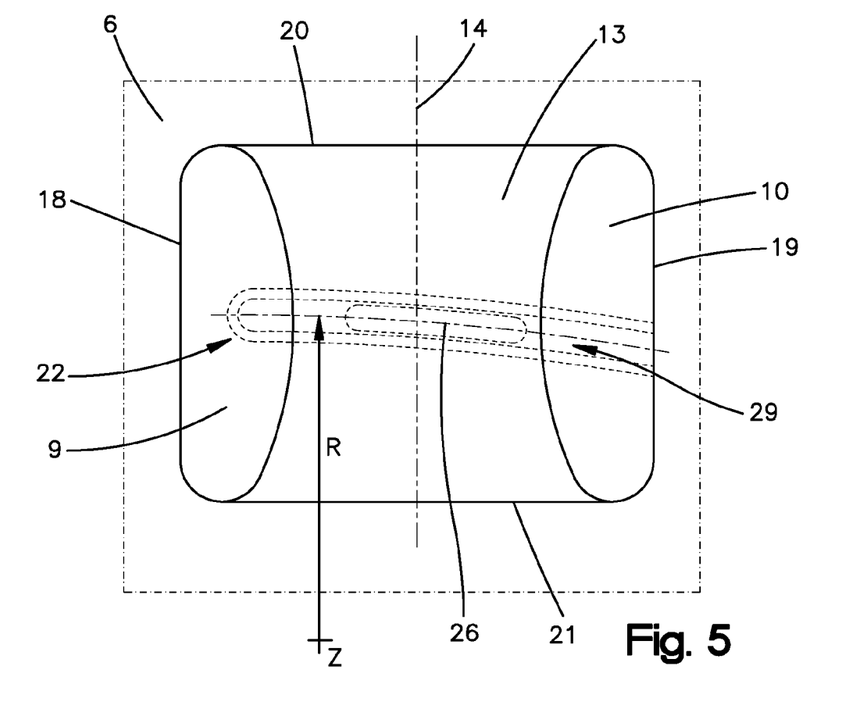
FIG. 5 is a top view of the embodiment shown in FIGS. 3 and 4.

The form of embodiment of the intervertebral implant 1 shown in the FIGS. 3 through 5 differs from the form of embodiment shown in the FIGS. 1 and 2 by the fact that the locking means 29, the male and the female dovetail guides 24;25 and the recesses for the gripping elements of a surgical instrument 35 (FIG. 7) are conformed in a different manner. The dovetail guides 24 are conformed so that their longitudinal axis 26 (FIG. 5) is curved. In order to also fasten the inserts 3;4, after the intervertebral implant 1 has been implanted, in a direction parallel to the base surfaces 15 with respect to the center piece 5, locking means 29, which are capable of being snapped into each other, are provided between each of the two male dovetail guides 24 and each of the two female dovetail guides 25.

Moreover, some first oval recesses 27 coming from the dorsal side surfaces 21 and penetrating into the sidebars 10, and second oval recesses 28 coming from the second side surfaces 19—which are set on the right side, if viewed from the dorsal side—and penetrating into the sidebars 10 are provided on the inserts 3;4. In the form of embodiment pictured here, the first and second oval recesses 27;28 are—if viewed from the dorsal side—inserted into the right-hand sidebars 10 of the two inserts 3;4. These first and second oval recesses 27;28 are suitable for receiving the gripping elements of a surgical instrument 35 (FIG. 7).

Figure 6:
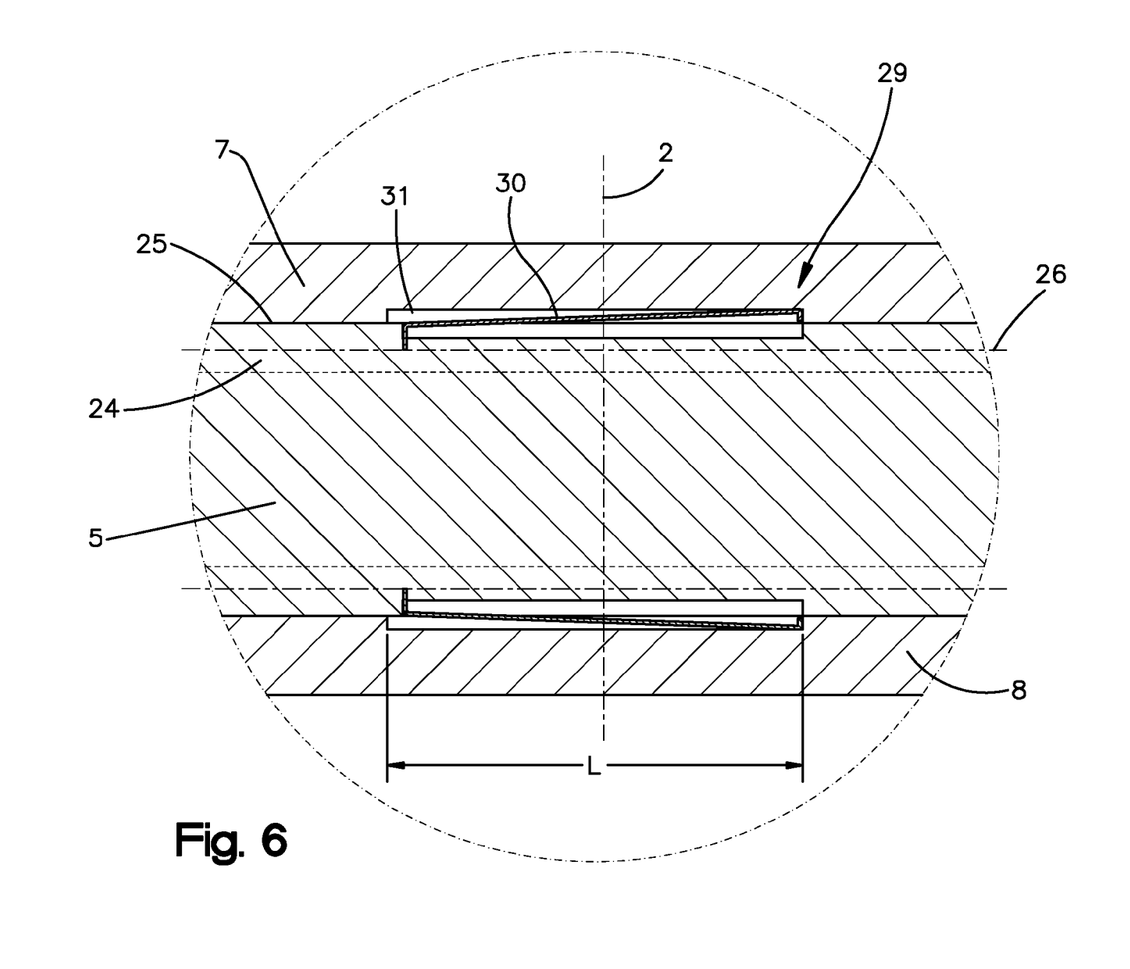
FIG. 6 is an enlarged cross-sectional view taken from circle A of FIG. 4.

As illustrated in FIG. 6, the locking means 29 essentially comprise a spring element 30 capable of being snapped into a recess 31, which is, in the form of embodiment pictured here, conformed like a leaf spring fastened to the center piece 5. The recess 31 is set on the female dovetail guide 25, and exhibits, in a direction parallel to the longitudinal axis 26 of the dovetail guides 24;25, a length L sized so that the spring element 30 snaps into the recess 31 when, at the time of pushing it in between the inserts 3;4 across the central axis 2, the center piece 5 has reached its final position with respect to the inserts 3;4. In the form of embodiment pictured here, the center piece 5 is held in position by the closed female dovetail guides 25 acting in a direction toward the first lateral side surfaces 18, and by the spring element 30 acting in a direction toward the second lateral side surfaces 19.

Figures 7, 8:
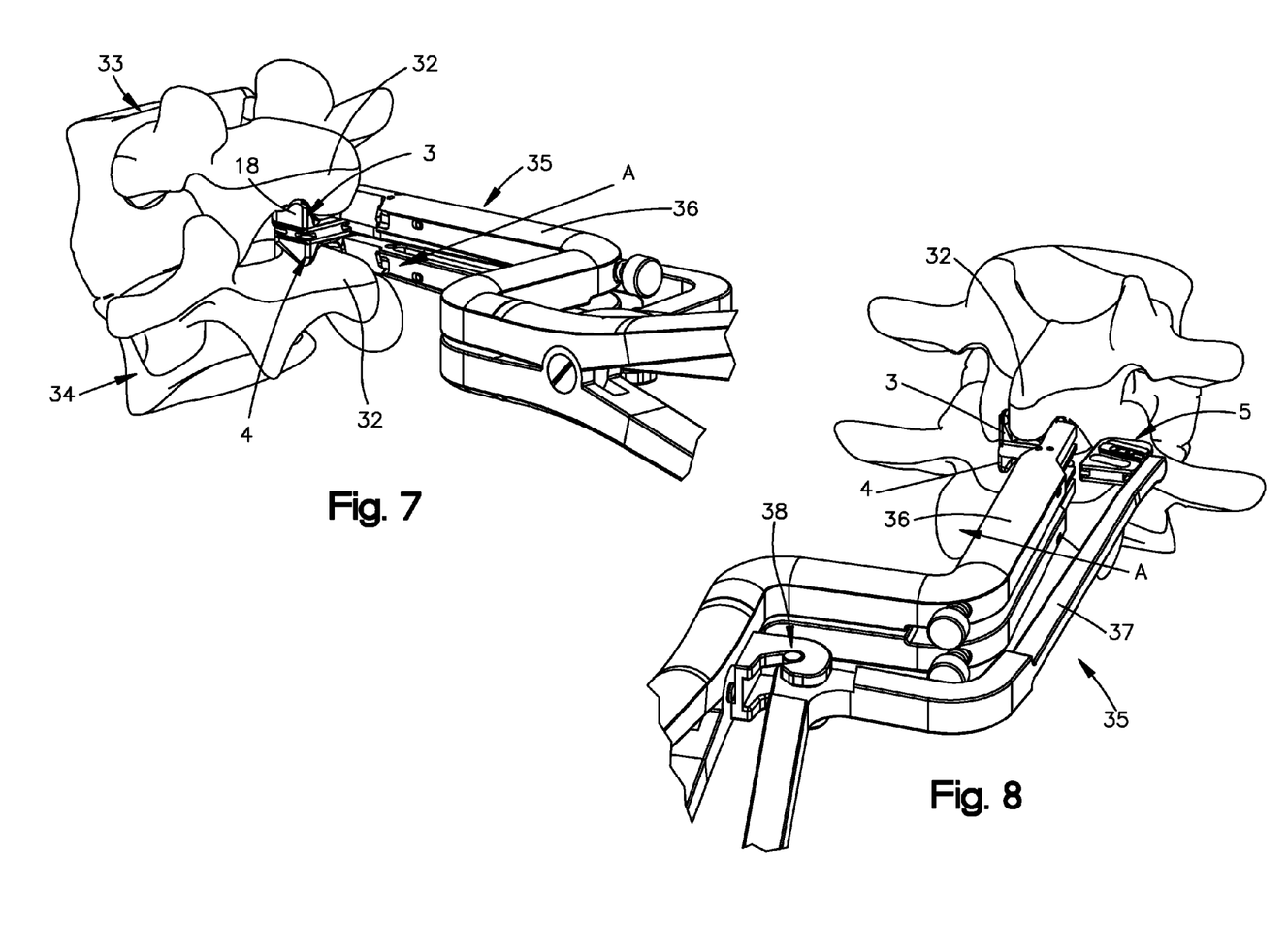
FIG. 7 is a perspective view of the two inserts of one embodiment of the intervertebral implant during implantation.
FIG. 8 is a perspective view of one embodiment of the intervertebral implant during insertion of the center piece.
Figure 10:
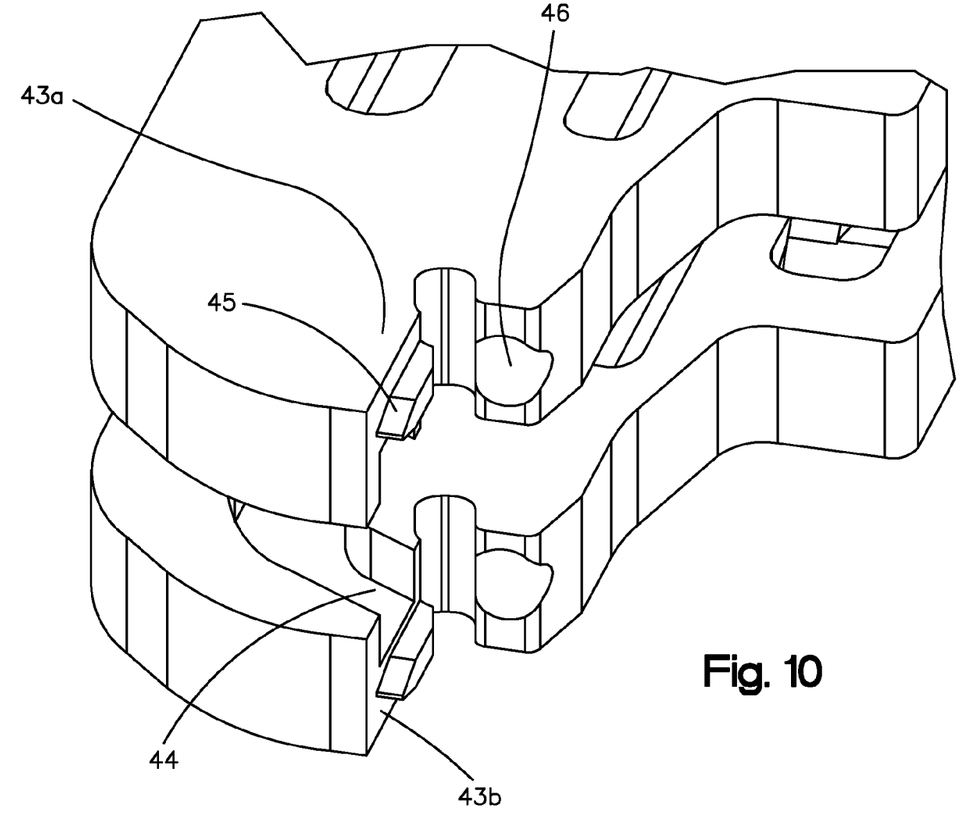
FIG. 10 is an enlarged view taken from circle II of FIG. 9.

FIGS. 7 and 8 help illustrate the following operating process for implanting the intervertebral implant 1:

(a) making a one-sided incision at the vertebral bodies 33;34 to be treated;

(b) distracting the vertebral bodies 33;34 to be treated by using a tongue (not shown) capable of passing through the lateral incision and coming into contact with the spinal processes 32 of the two vertebral bodies 33;34;

(c) introducing the two inserts 3;4 by passing a holding tongue 36 (FIGS. 7-10) through the lateral incision whereby, in the form of embodiment of the intervertebral prosthesis shown here, the inserts 3;4 are introduced from the right side in the direction of arrow A into the intermediate spaces between the spinal processes 32 of the two vertebral bodies 33;34 to be treated. For this purpose, the free extremities of the holding tongue 36 are anchored in the oval recesses 27;28 (FIG. 3) or in the grooves 42 (FIG. 1), so that the two inserts 3;4 can be pushed, with their first lateral side surfaces 18 facing forward, into the intermediate space of the spinal processes 32;

(d) introducing the center piece 5 from the side, by using the gripping lever 37 (FIGS. 7 and 8) or passing through the access channel 44 (FIGS. 9 and 10);

(e) generating an initial stress on the center piece 5 by slightly distracting the two inserts 3;4 with the holding tongue 36;

(f) releasing the fastening of the free extremities of the holding tongue 36 from the two inserts 3;4;

(g) removing the holding tongue 36; and (h) closing the incision.

FIGS. 9 and 10 show an embodiment of the surgical instrument 35 which is suitable for the embodiment of the intervertebral implant shown in the FIGS. 1 and 2. The gripping elements 43a;43b are fitted at their free extremities with rises 45 which can made to engage the grooves 42 on the lateral side surfaces 18;19 of the inserts 3;4.

After carrying out process step d above, the screws 40 are pushed through the openings 46 parallel to the channel axes 14 and into the sidebars 10 of the inserts 3;4.

In the form of embodiment of the surgical instrument shown in the FIGS. 7 and 8, according to the process step (d), the center piece 5 is pushed between the inserts 3;4 not by passing through an access channel 44, but by using a gripping lever 37, so that the following process steps should be carried out after process step (c):

(d') introducing a holding tongue 36 through the lateral incision, while the center piece 5 is gripped in the front end of the gripping lever 37;

(d") introducing the center piece 5 between the inserts 3;4 from the side by using the gripping lever 37; to simplify the execution of this step, the gripping lever 37 can be carried on the holding tongue 36 by a hinge 38 (FIG. 8) in a rotating manner;

(e) generating an initial stress on the center piece 5 by slightly distracting the two inserts 3;4 with the holding tongue 36;

(f) releasing the attachment of the free ends of the holding tongue 36 from the two inserts 3;4;

(g) removing the holding tongue 36; and (h) closing the incision.

The present invention has been described in connection with the preferred embodiments. These embodiments, however, are merely for example and the invention is not restricted thereto. It will be understood by those skilled in the art that other variations and modifications can easily be made within the scope of the invention as defined by the appended claims, thus it is only intended that the present invention be limited by the following claims.

We claim:

1. An implant for implantation between the spinal processes of adjacent vertebral bodies, the implant comprising:

a central axis;

two U-shaped inserts set over each other with respect to the central axis, each insert having opposing base surfaces, first and second lateral side surfaces, a ventral side surface, a dorsal side surface, and a contact surface, the contact surface having a channel configured to receive a spinal processes of a vertebral body, each of the two U-shaped inserts including a female dovetail guide formed in the base surface thereof, the female dovetail guide extending from the first lateral side surface towards the second lateral side surface, the female dovetail guide being closed at the second lateral side surface; and a center piece insertable across the central axis between the base surfaces of the two U-shaped inserts, the center piece having first and second resting surfaces, each of the resting surfaces having a male dovetail guide extending therefrom for engaging the corresponding female dovetail guide formed on the base surfaces of the two U-shaped inserts such that, after the male dovetail guides are received within the female dovetail guides, the U-shaped inserts are fastened in a detachable manner to the center piece parallel to the central axis, and wherein the male and female dovetail guides are operative to be engaged or disengaged only via the first lateral side surface; the U-shaped inserts further including connecting means operative to fasten the U-shaped inserts to gripping elements of a surgical instrument, the connecting means being formed on the first lateral side surface, and a bore for threadably engaging a screw, the bore being located between the channel and the first lateral side surface, the screw configured to project into the female dovetail guide between the male dovetail guide received within the female dovetail guide and the first lateral side surface such that the male dovetail guide is prevented from passing out of the female dovetail guide by the screw.

2. The implant of claim 1 wherein the male and female dovetail guides are configured in a form-locking manner parallel to a transversal axis set across the central axis and crossing the ventral and dorsal side surfaces.

3. The implant of claim 1 wherein the male and female dovetail guides are configured in a form-locking manner parallel to the central axis.

4. The implant of claim 1 wherein the male and female dovetail guides have longitudinal axes running across a transversal axis set across the central axis and crossing the ventral and dorsal side surfaces.

5. The implant of claim 1 wherein the male and the female dovetail guides are tapered toward the second lateral side surface.

6. The implant of claim 1 wherein a longitudinal axis of the male and female dovetail guides is curved.

7. The intervertebral implant of claim 1 wherein a longitudinal axis of the male and female dovetail guides is straight.

8. The implant of claim 1 wherein the implant is elastically deformable.

9. The implant of claim 8 wherein the implant has a progressive spring characteristic curve.

* * * * *